(12) United States Patent
Haines et al.

(10) Patent No.: US 6,689,999 B2
(45) Date of Patent: Feb. 10, 2004

(54) ILLUMINATION APPARATUS UTILIZING LIGHT EMITTING DIODES

(75) Inventors: Joshua Paul Haines, Auburn, NY (US); Stephen Frazer Belafonte, Sheffield (GB); Charles Henry Hurst Willis, Doncaster (GB); Nicholas Andrew Rixham, Sheffield (GB)

(73) Assignee: Schott-Fostec, LLC, Auburn, NY (US)

( * ) Notice: Subject to any disclaimer, the term of this patent is extended or adjusted under 35 U.S.C. 154(b) by 146 days.

(21) Appl. No.: 09/872,642

(22) Filed: Jun. 1, 2001

(65) Prior Publication Data

US 2002/0179816 A1 Dec. 5, 2002

(51) Int. Cl.[7] .................................................. G01J 1/32
(52) U.S. Cl. ........................................ 250/205; 250/238
(58) Field of Search ................................ 250/205, 226, 250/238, 239, 214 P, 227.22; 356/73; 362/2, 11, 16, 18

(56) References Cited

U.S. PATENT DOCUMENTS

| | | | |
|---|---|---|---|
| 5,029,245 A | * | 7/1991 | Keranen et al. ............ 250/205 |
| 5,471,052 A | * | 11/1995 | Ryczek ....................... 250/226 |
| 5,783,909 A | | 7/1998 | Hochstein |
| 5,907,569 A | | 5/1999 | Glance et al. |
| 6,111,739 A | | 8/2000 | Wu et al. |
| 6,127,784 A | | 10/2000 | Grossman et al. |
| 6,153,980 A | | 11/2000 | Marshall et al. |
| 6,183,086 B1 | | 2/2001 | Neubert |
| 6,222,172 B1 | | 4/2001 | Fossum et al. |
| 6,232,724 B1 | | 5/2001 | Onimoto et al. |

* cited by examiner

Primary Examiner—Que T. Le
(74) Attorney, Agent, or Firm—Robert J. Sinnema; Bond, Schoeneck & King, PLLC

(57) ABSTRACT

A light emitting diode lighting apparatus that includes: a power supply for providing a fixed direct current; a light emitting diode head for emitting light; and a controller for adjusting the level of said light output on said head and compensating for efficiency altering effects of said light in said power head, whereby said controller receives signals for optical feedback stabilization, temperature compensation, and detection of short term current changes to adjust said light and efficiency.

19 Claims, 24 Drawing Sheets

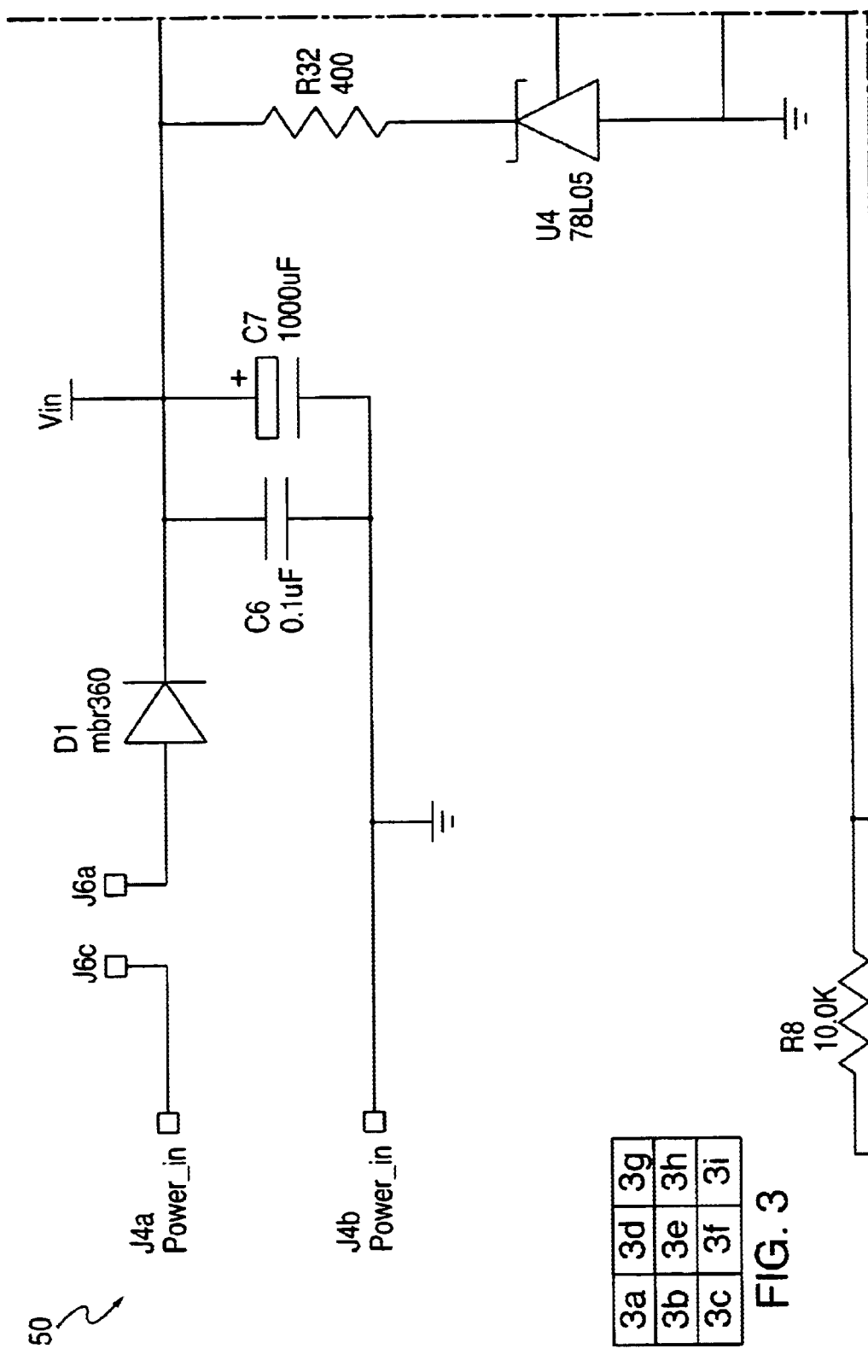

ILLUMINATION APPARATUS UTILIZING LIGHT EMITTING DIODES

BACKGROUND OF THE INVENTION

The present invention relates to a light emitting diode lighting system and more particularly to a light emitting diode array, which is used, for example, in machine vision identification and systems used to inspect production objects such as mechanical components, printed circuit boards, foodstuffs, and the like.

In the field of vision identification and inspection, through the use of a lighting system, a well-defined lighting system results in many benefits. Some of the benefits include, but are not limited to, simplification of the computer algorithms necessary for reliable object identification and reduction of erroneously rejected objects. There are benefits with minimizing the space, cost and maintenance of the lighting system. Well-defined lighting systems result in efficiencies during operation and manufacture.

Light emitting diode (LED) array light sources are widespread in use in a variety of different signaling and lighting applications. Typical uses of LED arrays include image sensors, inspection of parts, luminaries, and the like. It is generally advantageous to connect all of the LEDs in series because the result is a high-voltage and low-current load that is more economical than low-voltage and high-current connection. However, the high-voltage and low-current approach has a problem. For example, if one of the LEDs that are connected in series fails by an open-circuit condition then the rest of the LEDs connected in series will not operate. Consequently, LED arrays incorporate a combination of series connected and parallel connected strings of LEDs to avoid failure of the entire array. However, this solution is complex to manufacture, not as economical as an all series LED array, and creates an array with a fluctuating light output.

In one prior art application a light emitting diode (LED) array connected in series has an active shunt arrangement for sensing a failure of one or more of the LEDs, and for shunting current that would have otherwise flowed through a failed LED. This scenario maintains a flow of current through the remaining LEDs. The active shunt arrangement includes several active shunts connected in parallel across respective ones of the LEDs, and remote sense and digital logic for detecting an open-circuit condition of the normally closed circuit, and for sequentially activating the active shunts until the normally closed circuit has been restored to a closed-circuit condition. However, a problem associated with this arrangement is that it requires a complex arrangement of circuits and controls that require an individual circuit to sense a failure condition of an associated LED. Each active shunt is an active switching device connected in parallel with each LED that consumes more energy than a simple LED array connected in series, and produces fluctuations in the light output when the shunts are engaged.

The stability of the light field is important wherever thresholds need to be set, for example, in software, as part of the inspection criteria. Stability and efficiencies can be achieved by regulation of the power delivered to the light source, internal controls within the light source, or auto-feedback of the light field back to the camera or light source. What is needed are improved internal controls within the light source to regulate light level output, regulate the relative operating temperature and indicate the LED head forward voltage.

SUMMARY OF THE INVENTION

It is an aspect of the invention to regulate the temperature of LED arrays that increases the efficiency of the forward current.

It is another aspect of this invention to control the level of light output of LED arrays and compensate for efficiency altering effects on LED arrays.

A light emitting diode lighting apparatus includes a power supply with a fixed direct current, a light emitting diode head for emitting light, and a controller for adjusting the level of light to compensate for efficiency altering effects. The controller receives from the light emitting diode head signals for optical feedback stabilization, temperature compensation, and detection of short-term current changes to adjust said light and efficiency.

A light emitting diode (LED) head includes a body that is internally hollow for positioning a light emitting diode cluster inside and connected with a signal cable. The light emitting diode cluster is mounted on a platform for emitting a desired level of light. A photosensitive device that collects a representative amount of light from one or a number of LEDs, using the photocurrent generated as a regulation parameter signal to drive the LED cluster through an intelligent controller, is mounted on the platform but optically isolated from the LED cluster. Also mounted on the platform is a thermistor for monitoring temperature of the LED cluster, by generating an operating temperature signal to drive the LED cluster through an intelligent controller, with the thermistor located within the LED cluster. Furthermore, a LED failure detector that continuously monitors the current of the LED cluster is mounted on the platform, allows the detection of short term current changes, and provides a signal to drive the LED cluster through an intelligent controller. The system monitors head voltage and indicates a change in the head voltage due to LED failure. The platform is mounted inside the body and a plate and retaining ring secure the platform inside the body.

DETAILED DESCRIPTION OF THE INVENTION

While the present invention is described below with reference to a LED lighting array, a practitioner in the art will recognize the principles of the claimed invention are applicable in other applications.

Figure 1:
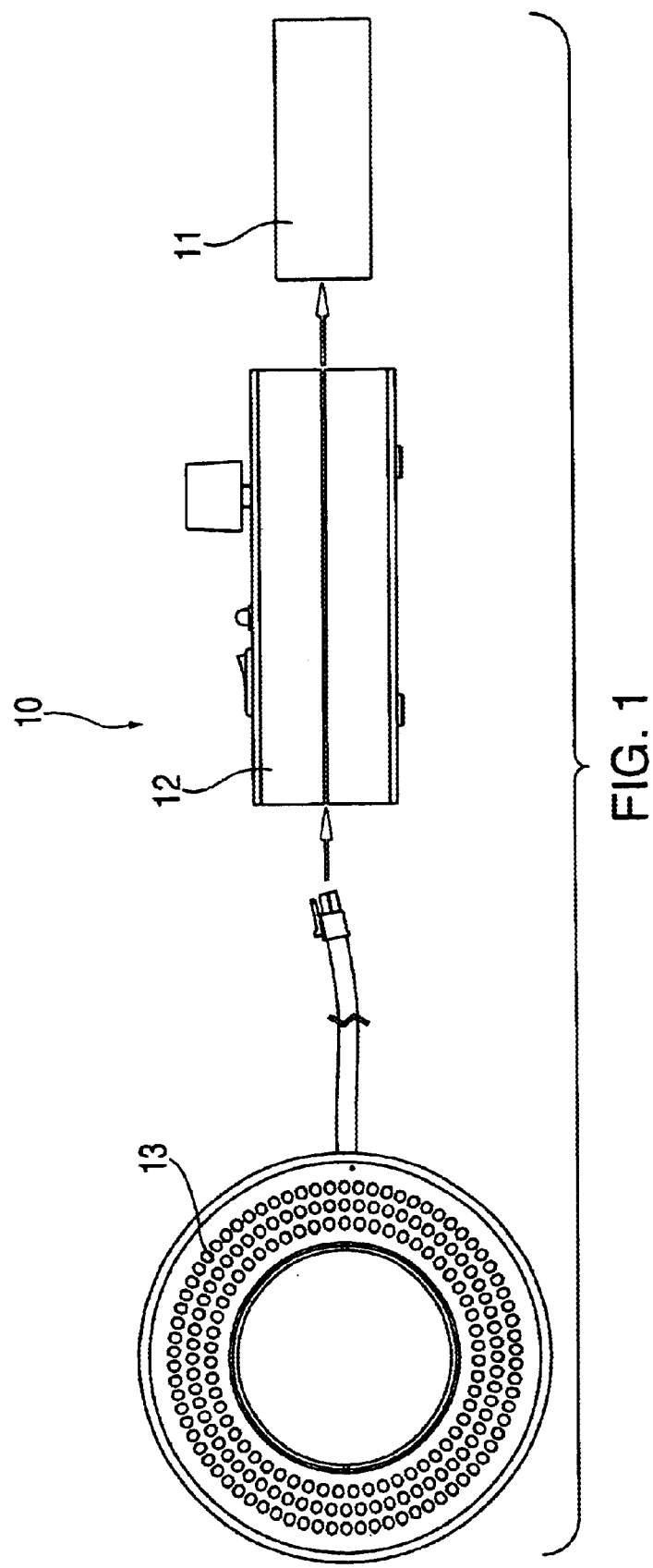
FIG. 1 is a diagram showing the preferred embodiment of the claimed invention.

Now referring to FIG. 1, apparatus 10 is a preferred embodiment of the invention and is shown powered by a fixed DC power supply 11, controlled by an intelligent controller 12, which operates a light emitting diode (LED) head 13. The power supply 11 is a fixed DC supply and may be purchased off the shelf but needs to provide about 12 v dc output. Examples of intelligent controllers available in the marketplace are the Universal, Pro LE, Ultra LX or Ultra LX Interface. The intelligent controller accepts a 12 v dc input and has switchable power resistors to limit the current going to any light emitting diode head 13 with color LED's. An intermediate alternative is the Pro LE controller that supplies a variable constant current to the LED head 13, and improves light output stability. The most complex solution is the Ultra LX Interface controller that also implements a variable constant current drive by an analog (0–5 v dc) input voltage. This unit makes available to the user three output analog voltages representing the LED light level output, the relative operating temperature of the LEDs, and the LED head forward voltage. The intended use of the Ultra LX Interface, as the intelligent controller 12, is with an integrator software package. It is known that LED efficiency is related to the operating temperature of the LED array (cluster). As the temperature increases the efficiency of forward current to light output decreases. This change in efficiency can be compensated for by a negative feedback loop that controls the LED head 13 drive current. The Ultra LX Interface that can be used as the intelligent controller 12 provides a positive feedback loop that efficiently controls the LED head 13 drive current.

Figure 2:
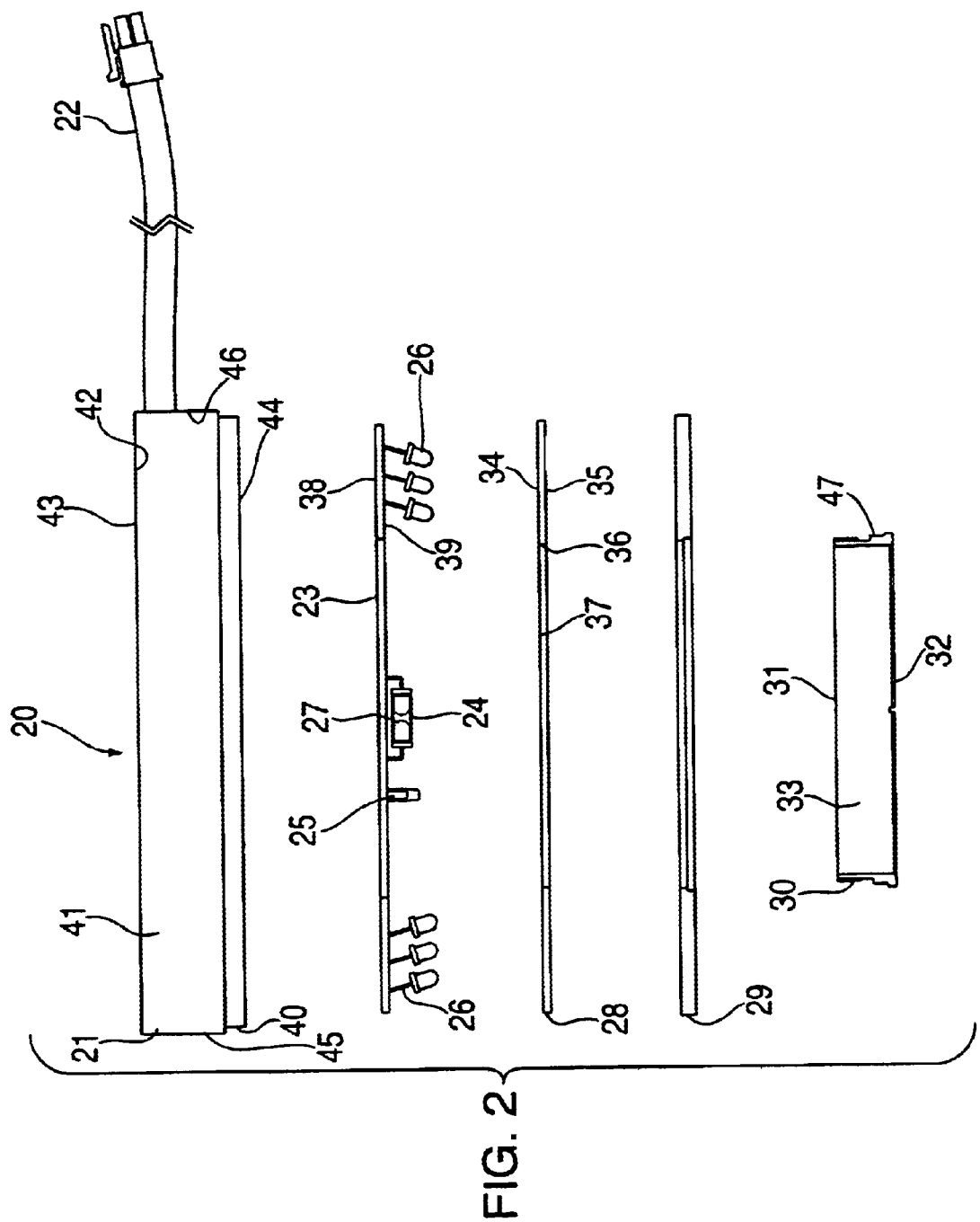
FIG. 2 is an assembly of the preferred embodiment of the claimed invention.
Figure 3B:
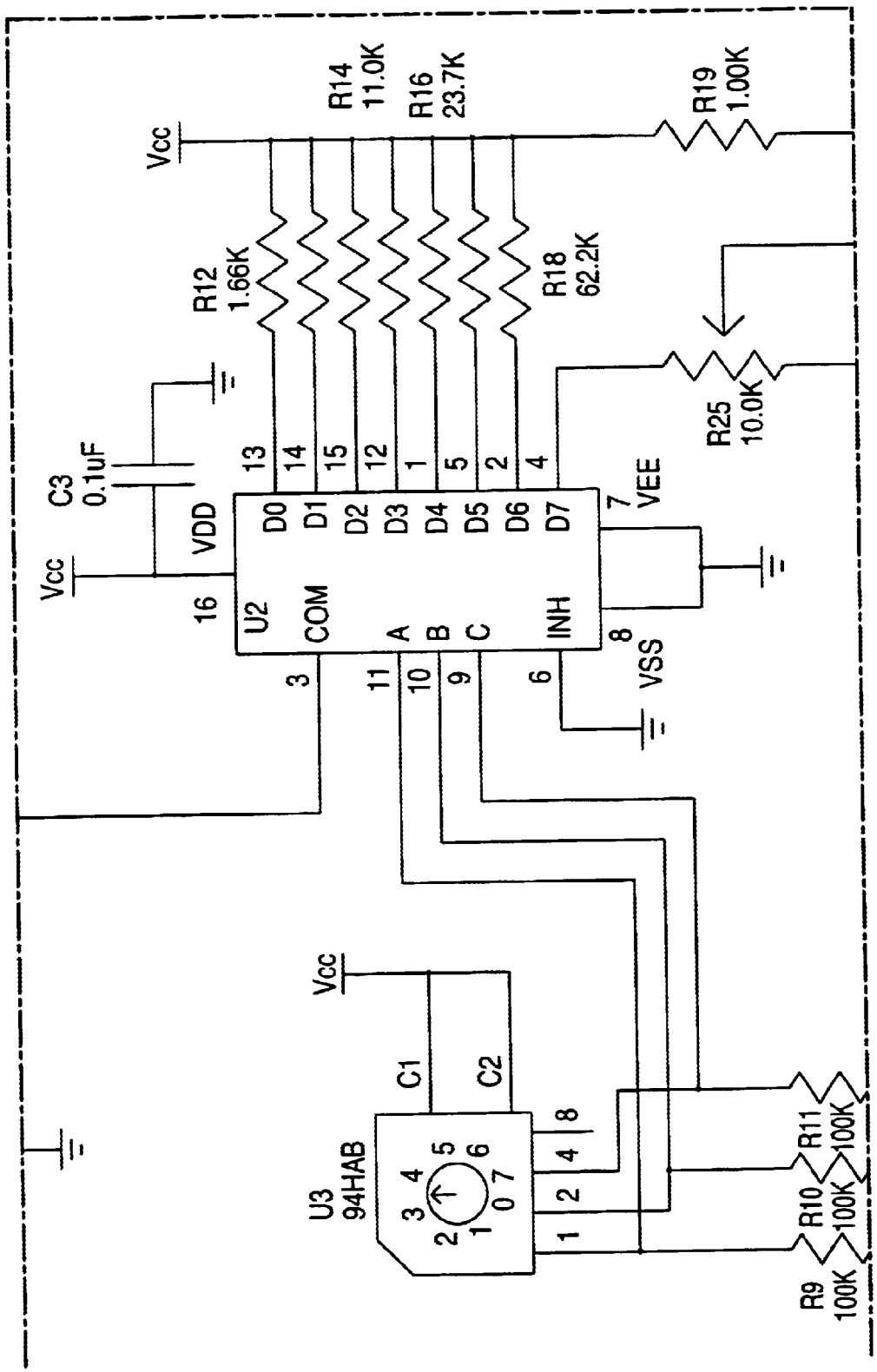
FIG. 3 is an electrical schematic of the preferred embodiment of the claimed invention.
Figure 3C:
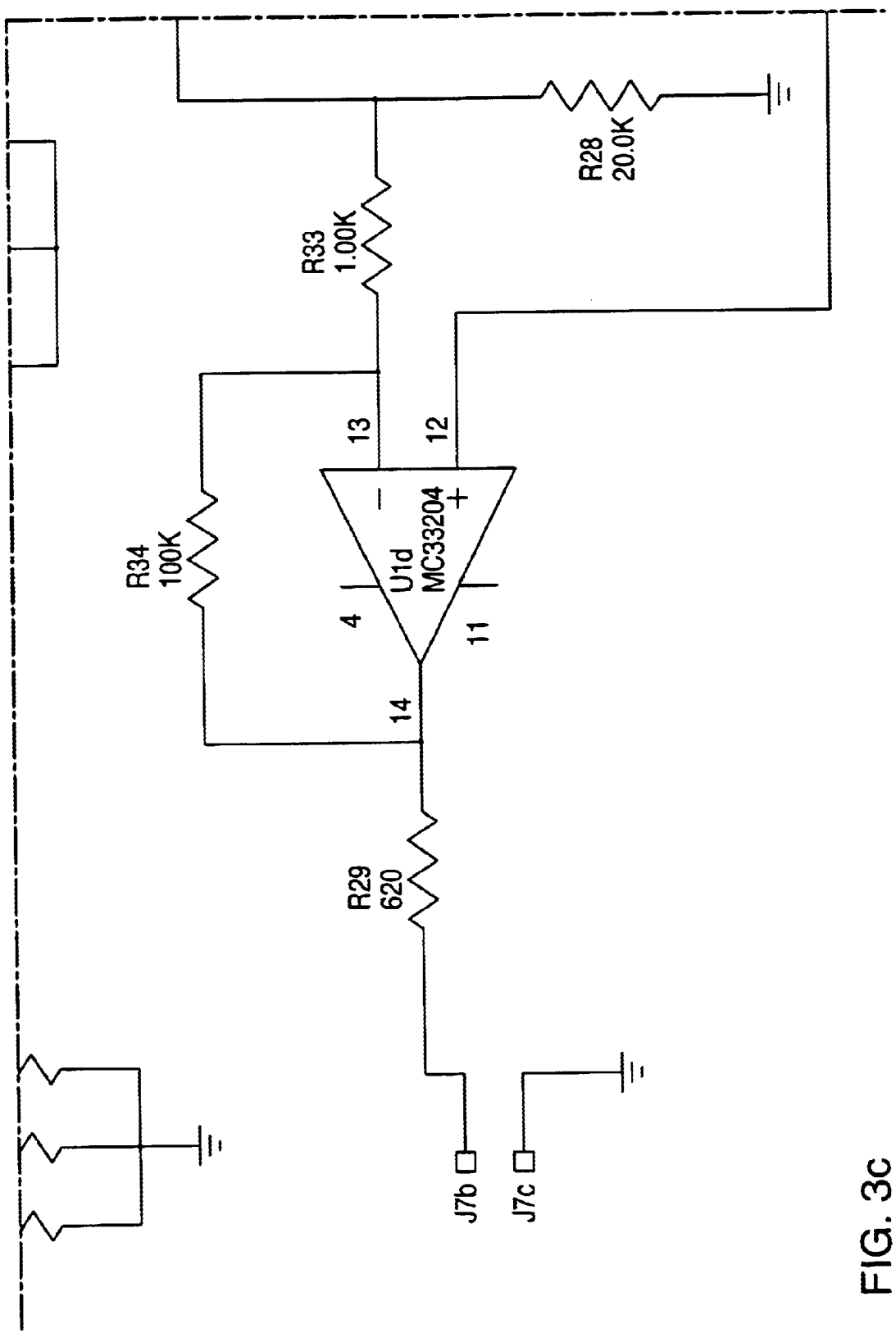
Figure 3D:
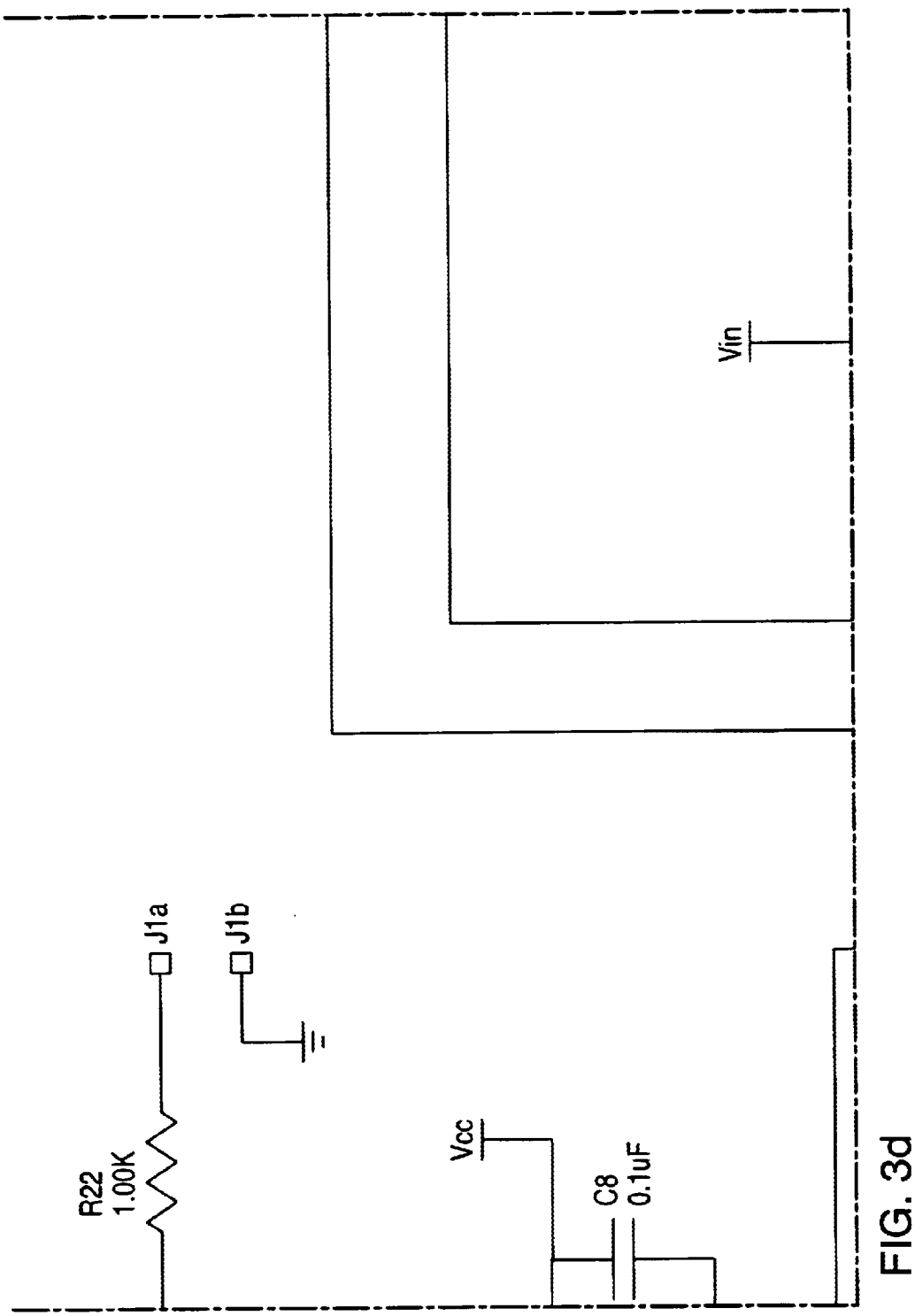
Figure 3E:
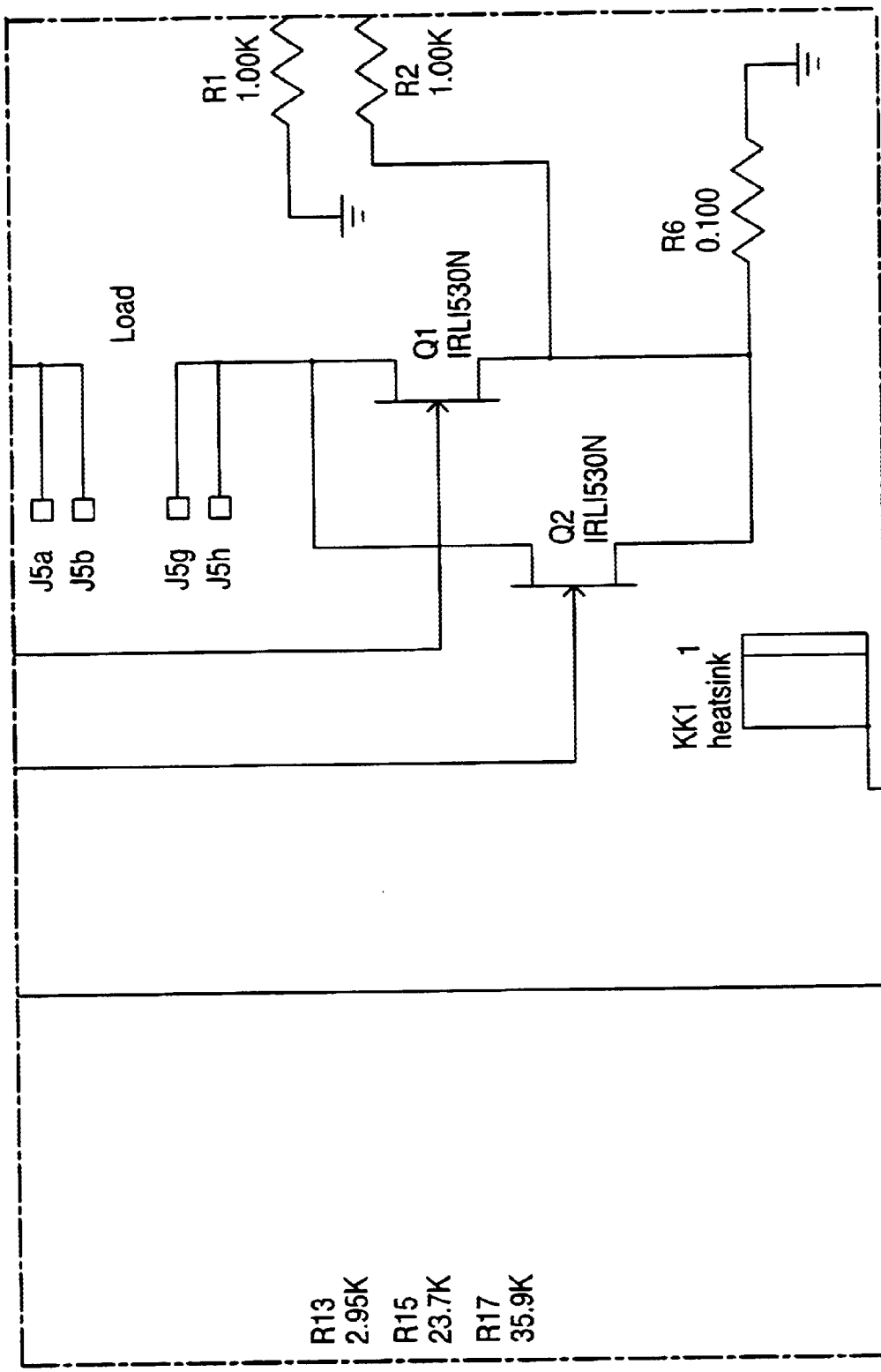
Figure 3F:
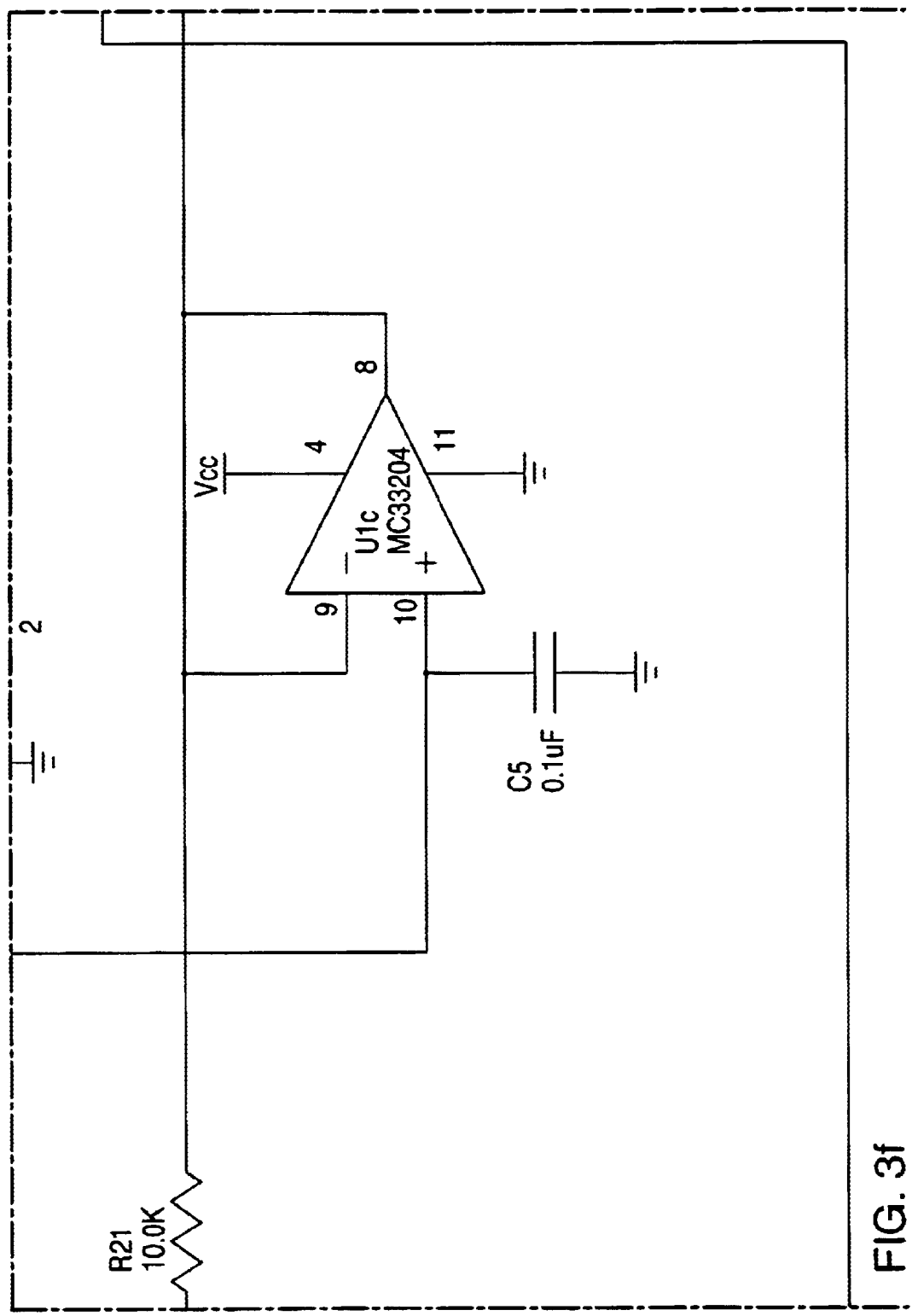
Figure 3G:
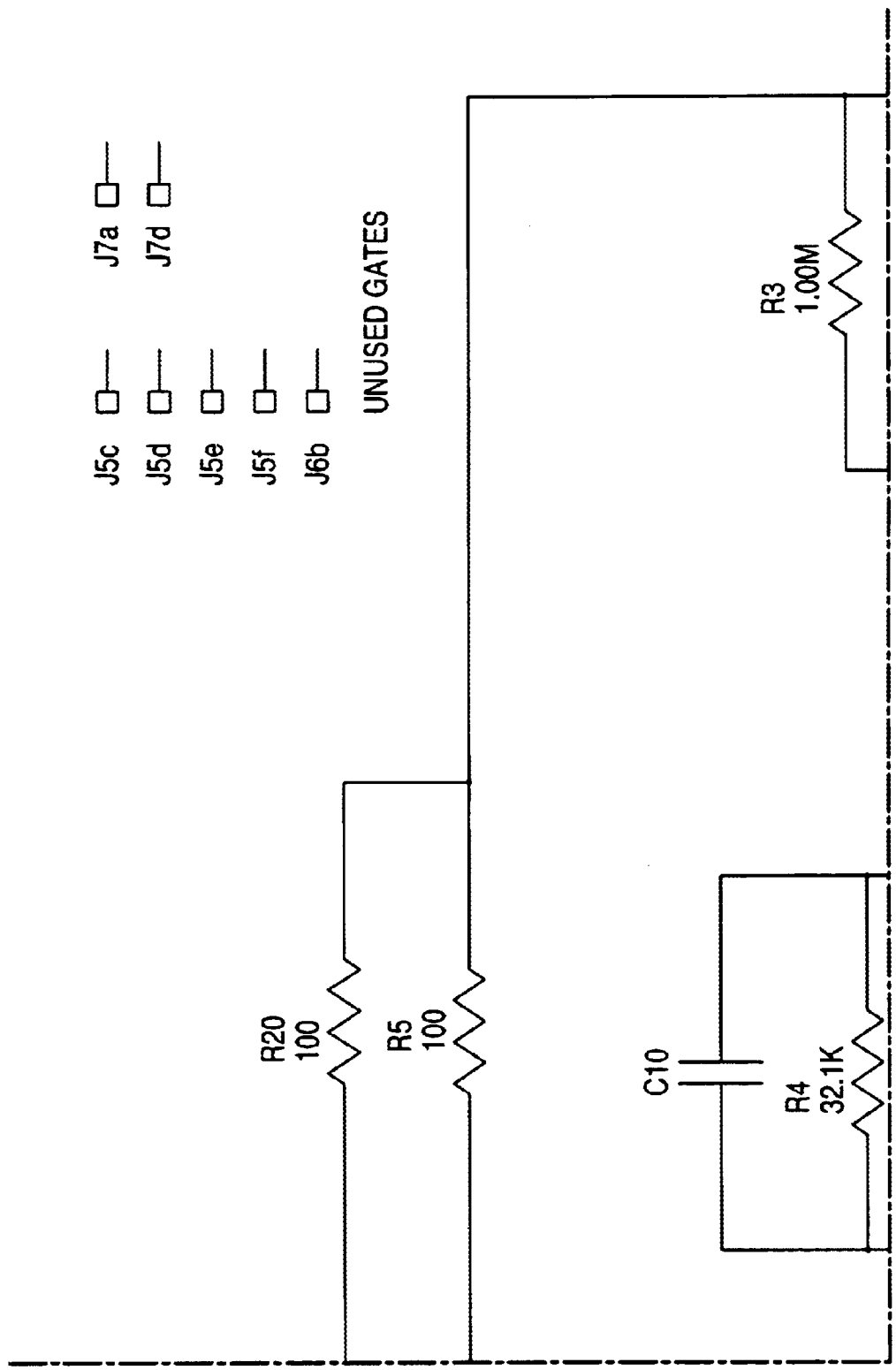
Figure 3H:
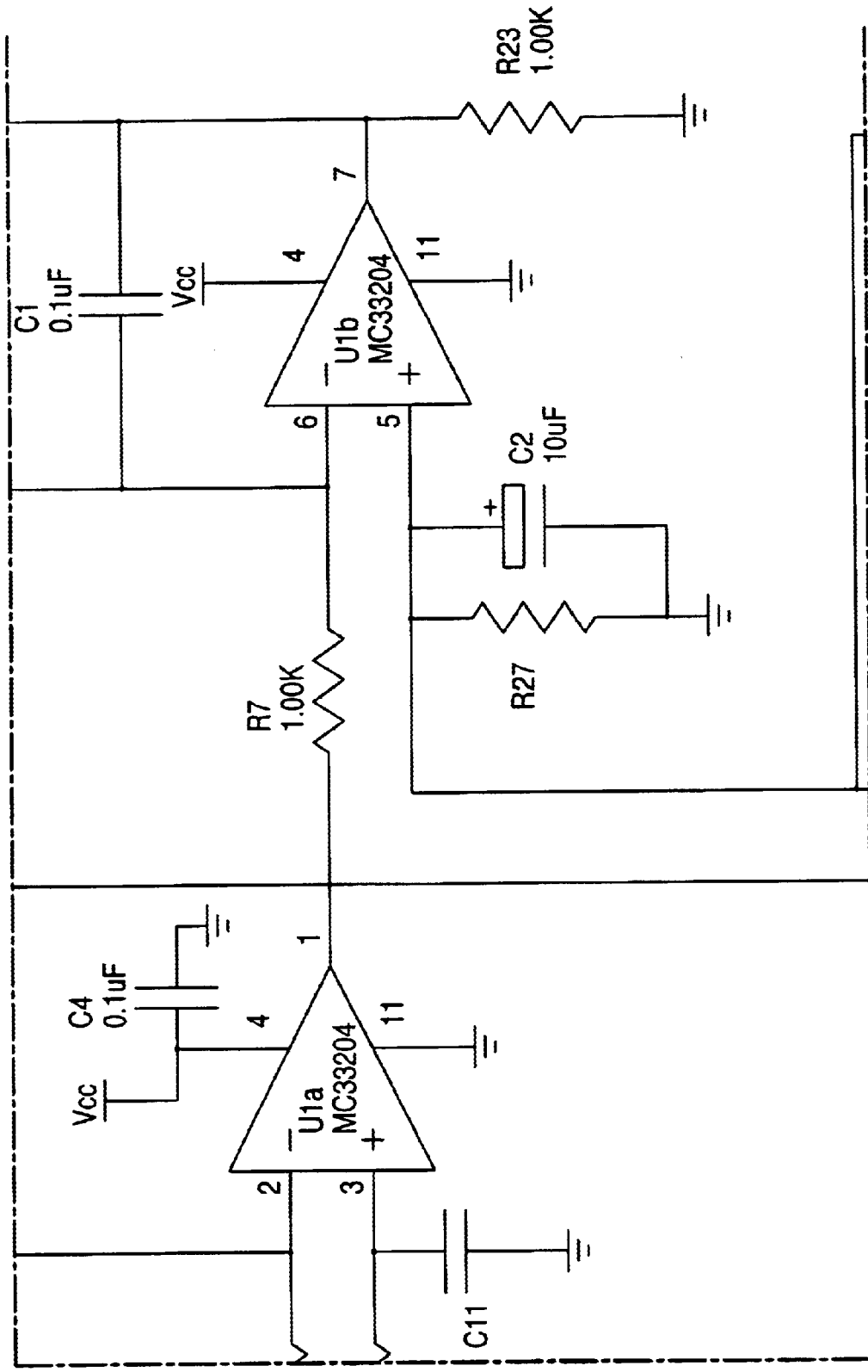
Figure 3I:
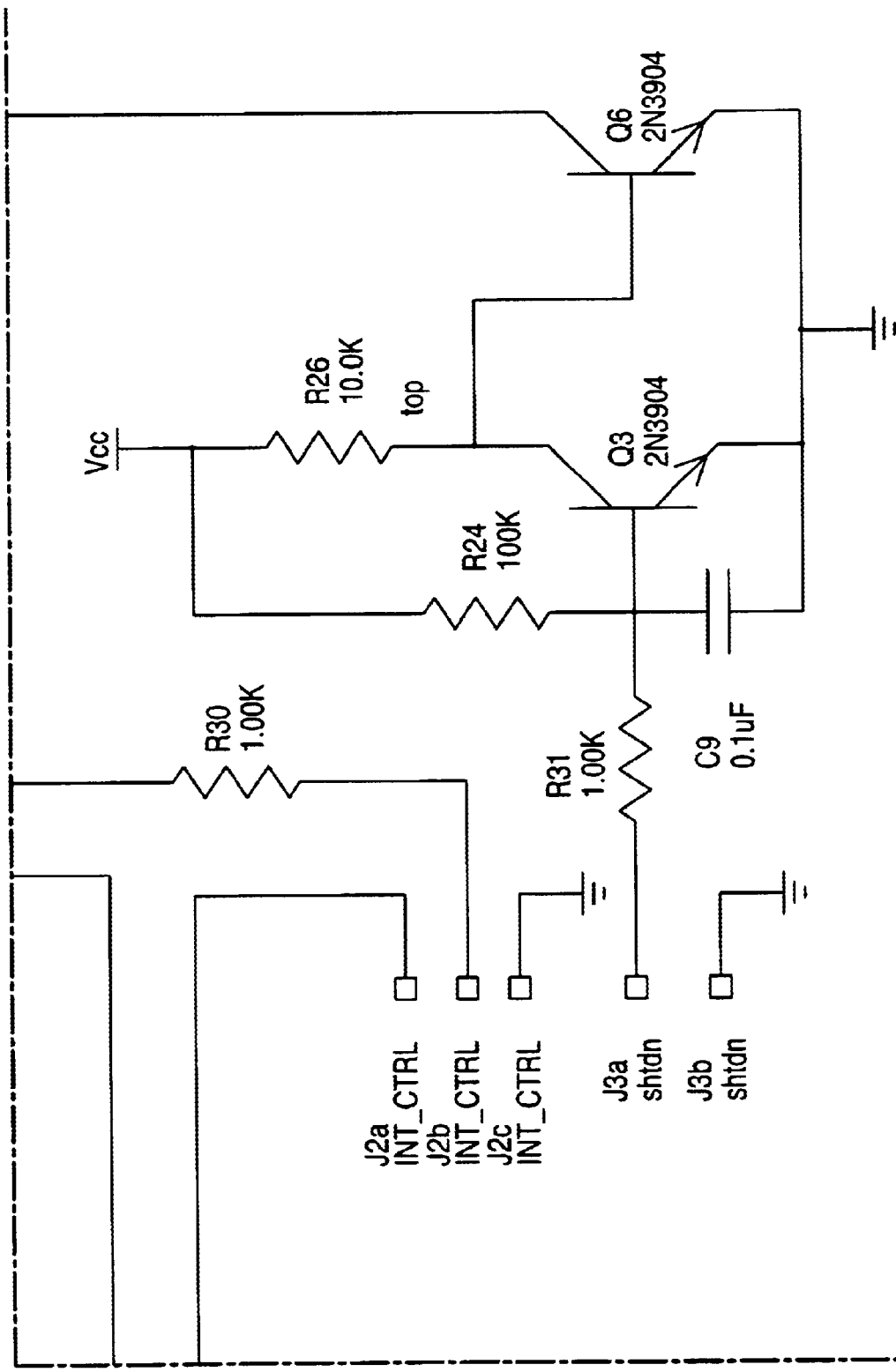
Figure 4A:
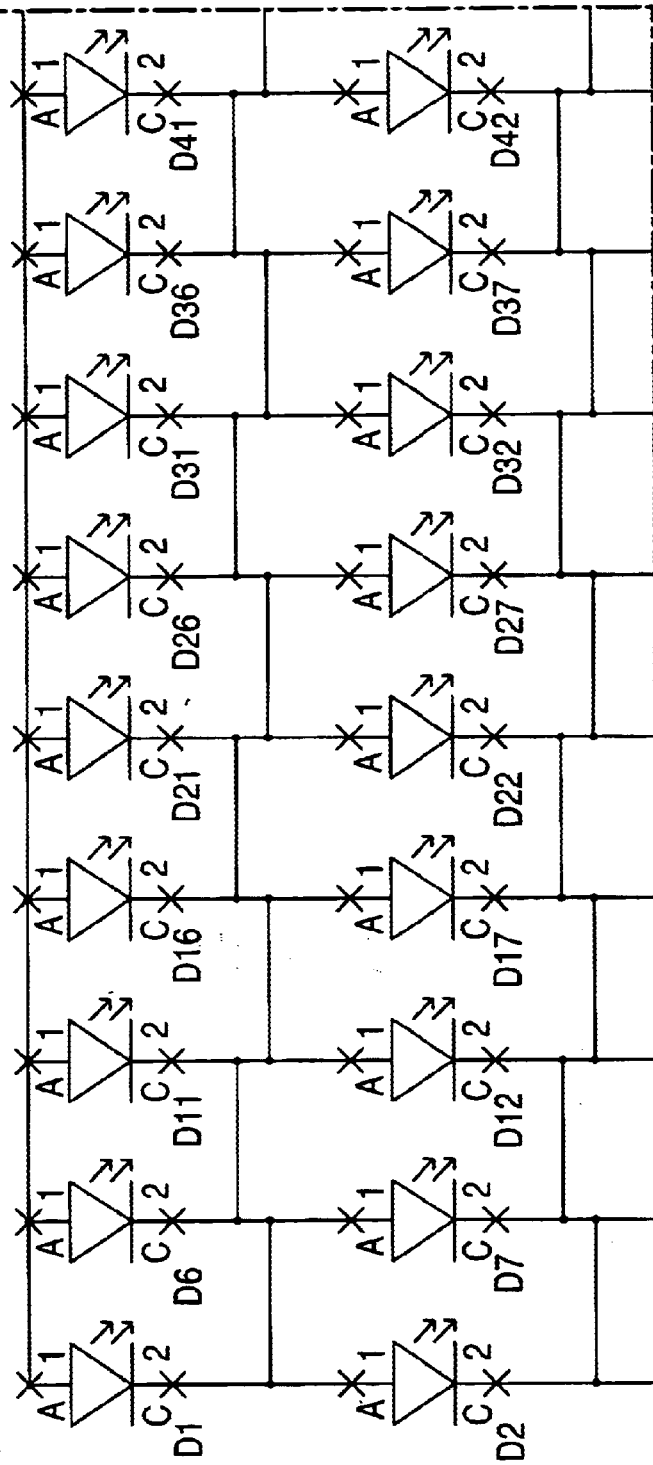
FIG. 4 is an electrical schematic of the light emitting diode cluster, of the preferred embodiment of the claimed invention.
Figure 4B:
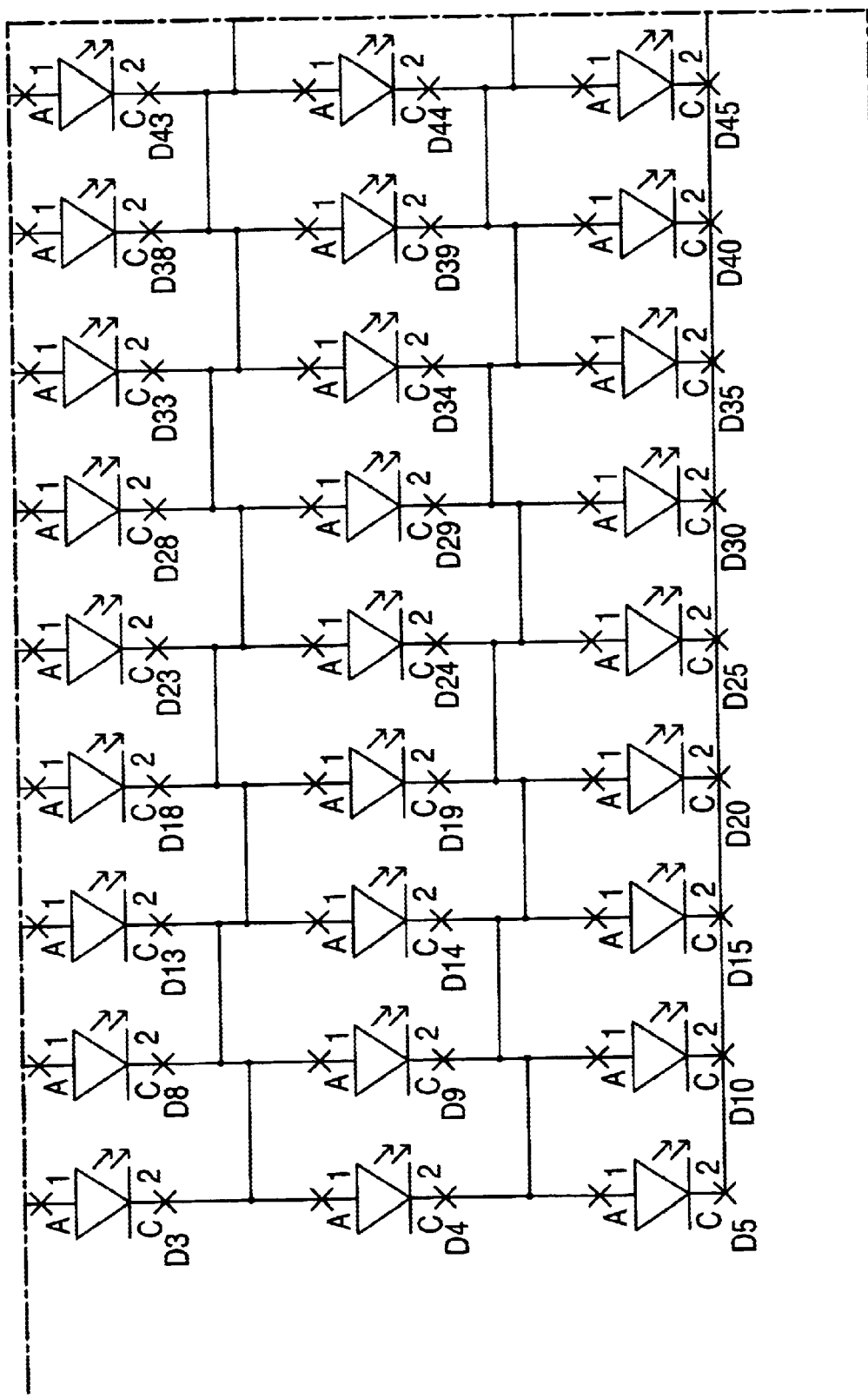
Figure 4C:
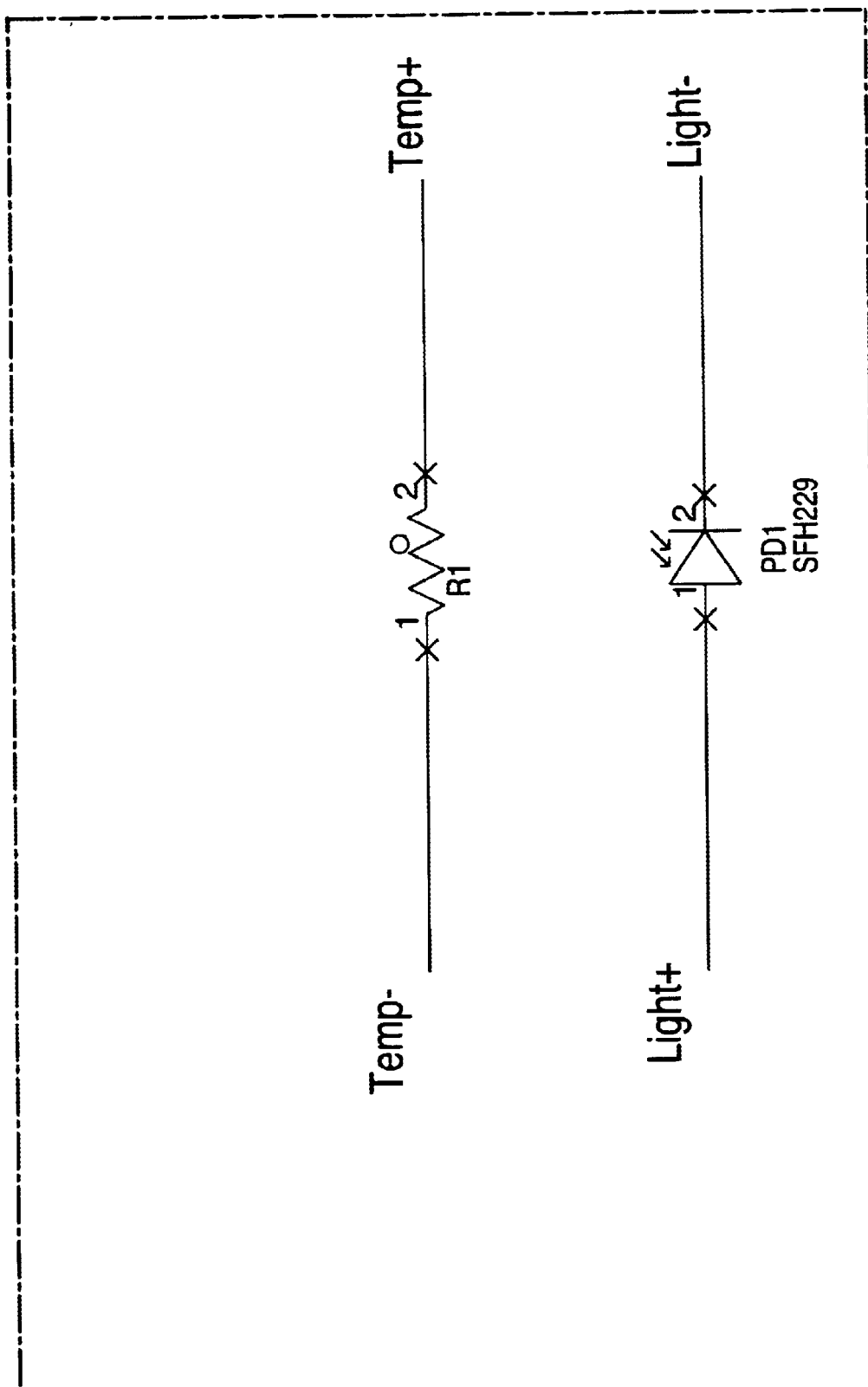
Figure 4D:
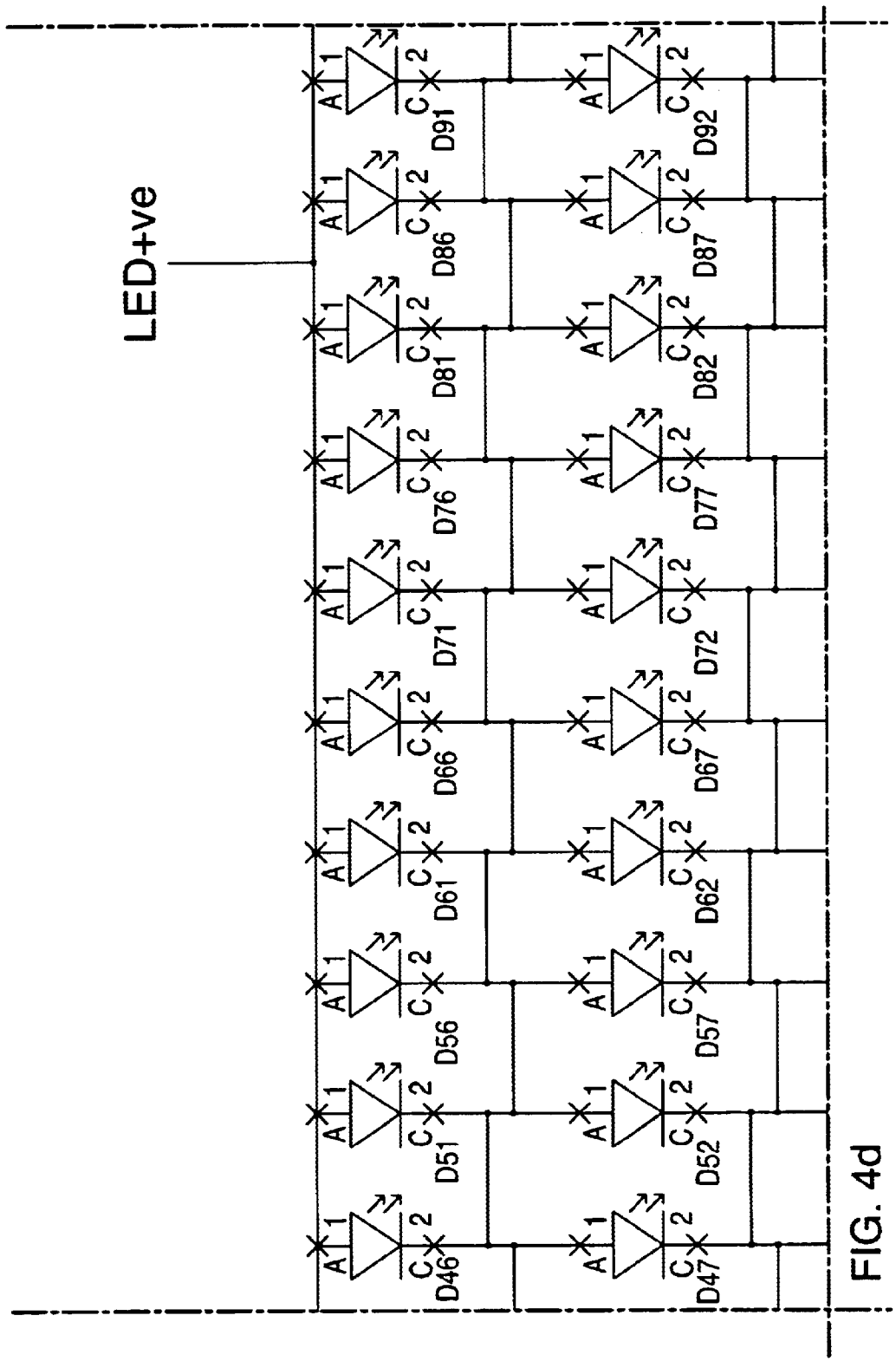
Figure 4E:
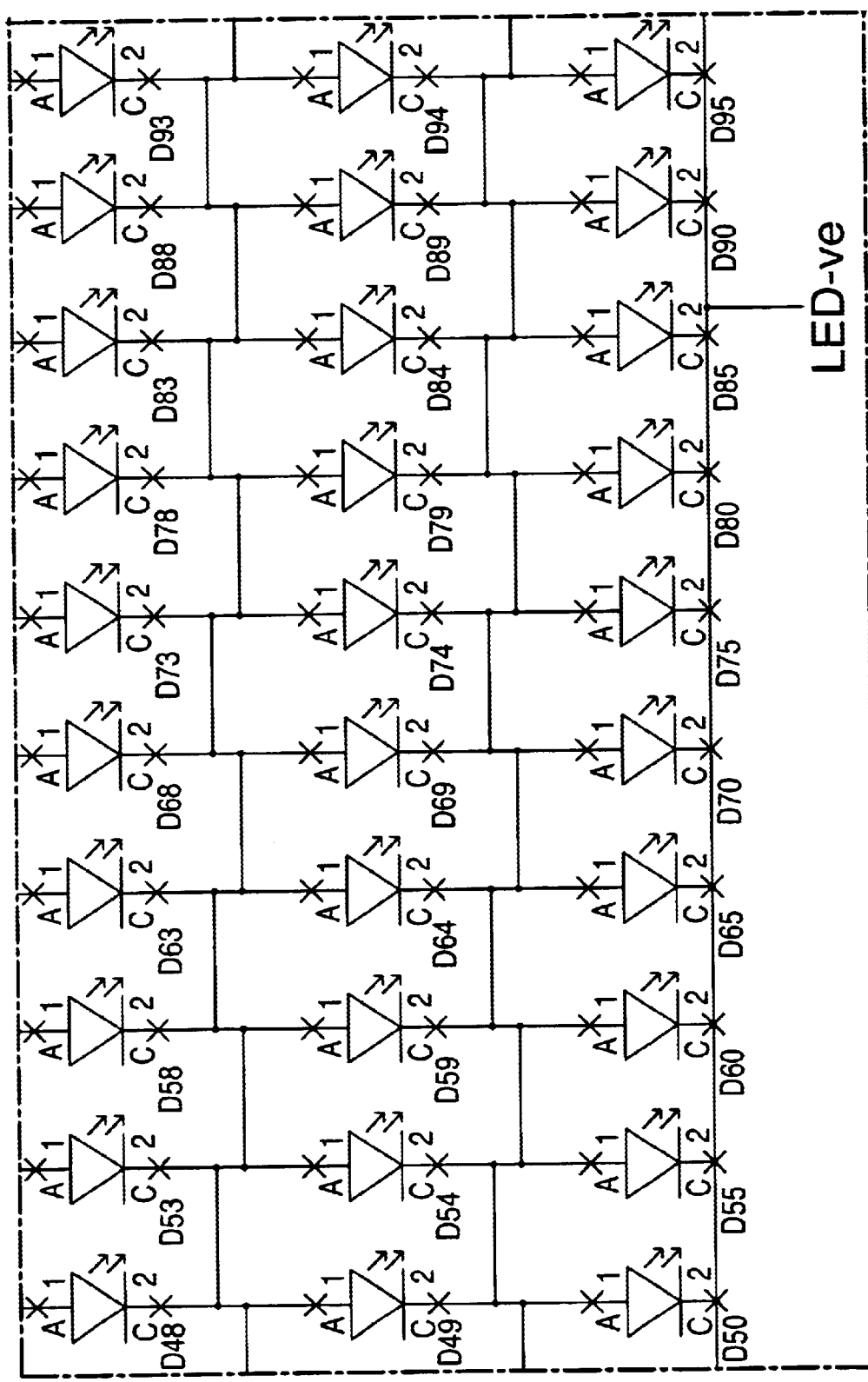
Figure 4F:
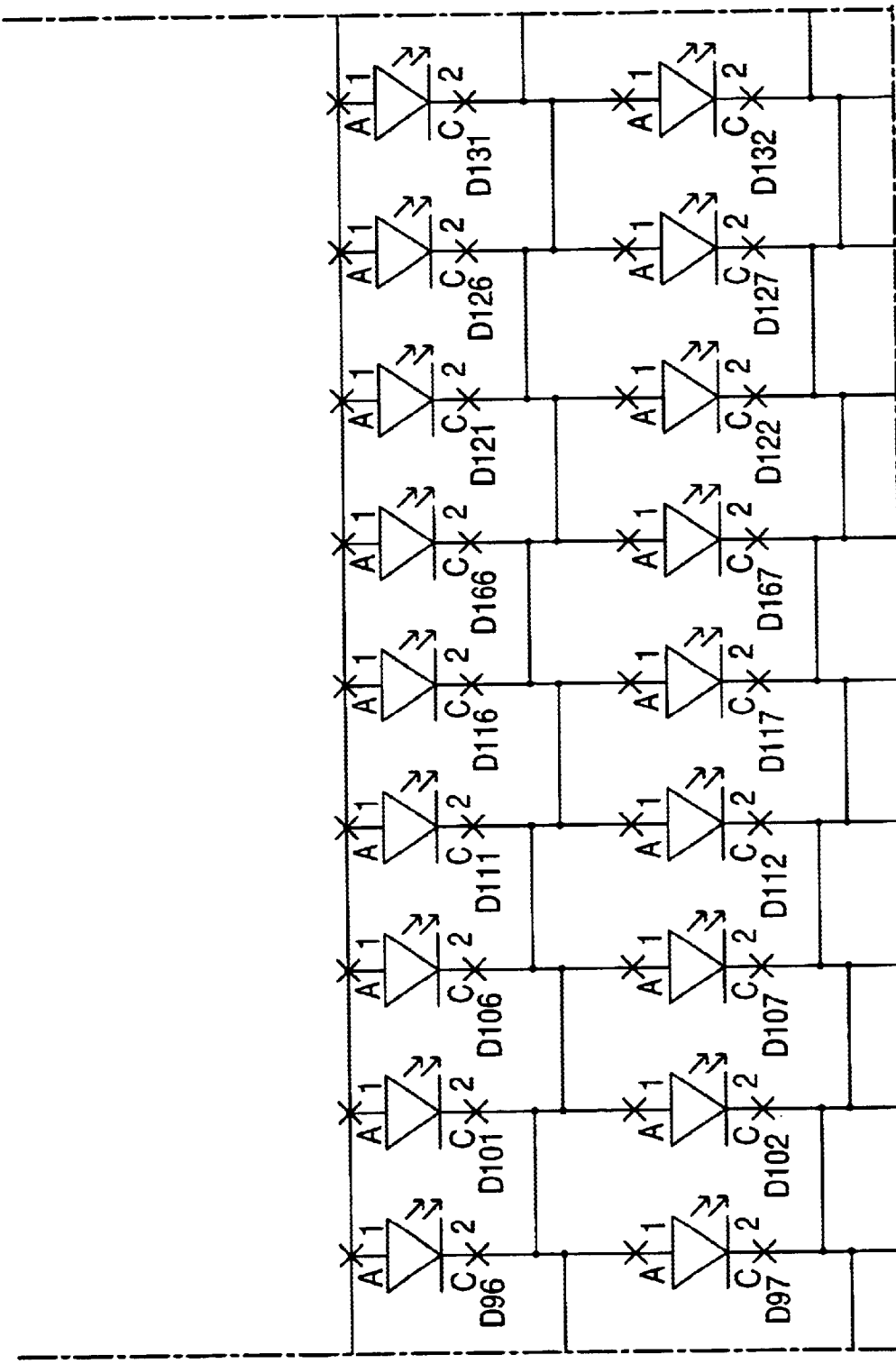
Figure 4G:
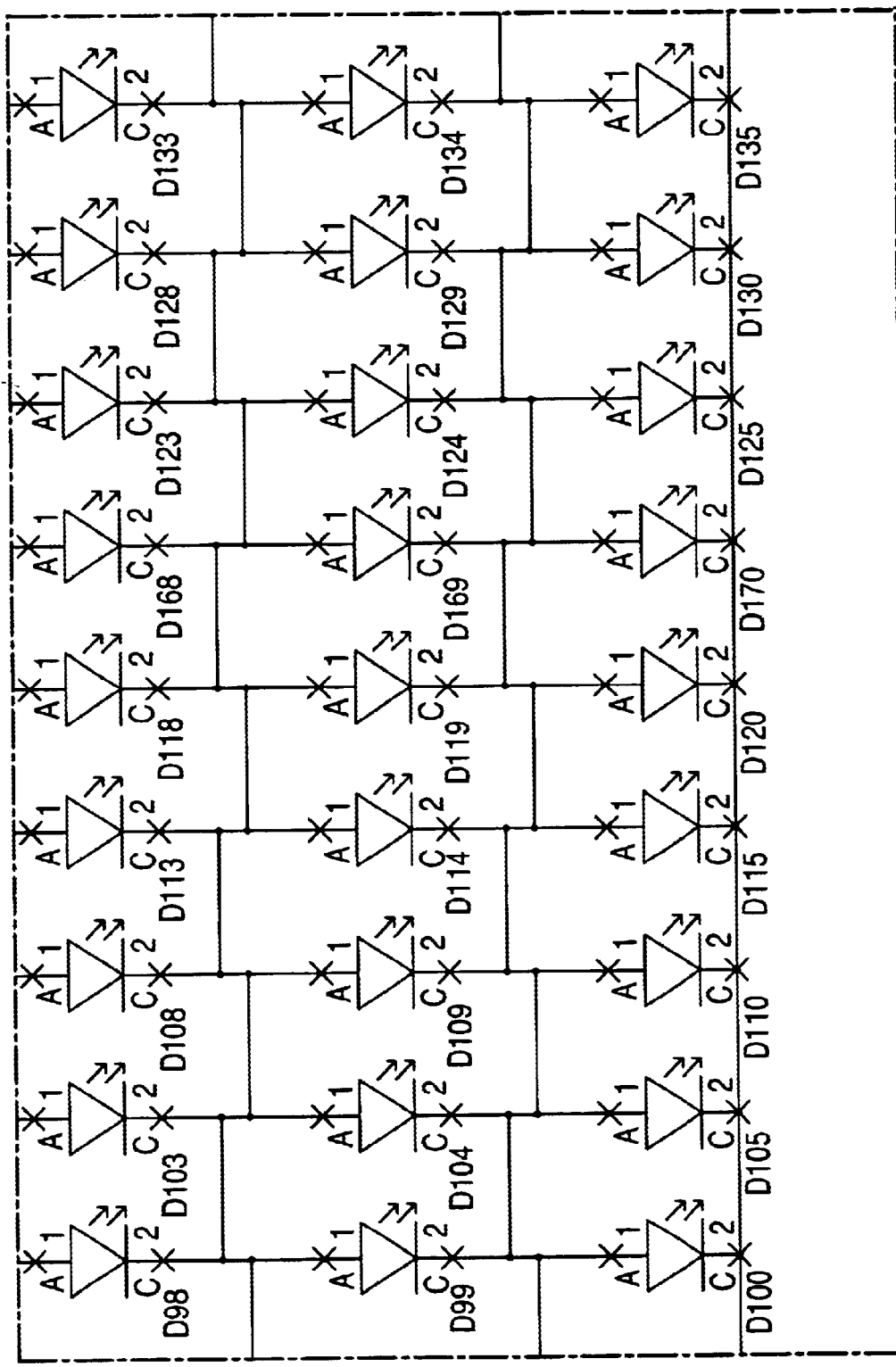
Figure 4H:
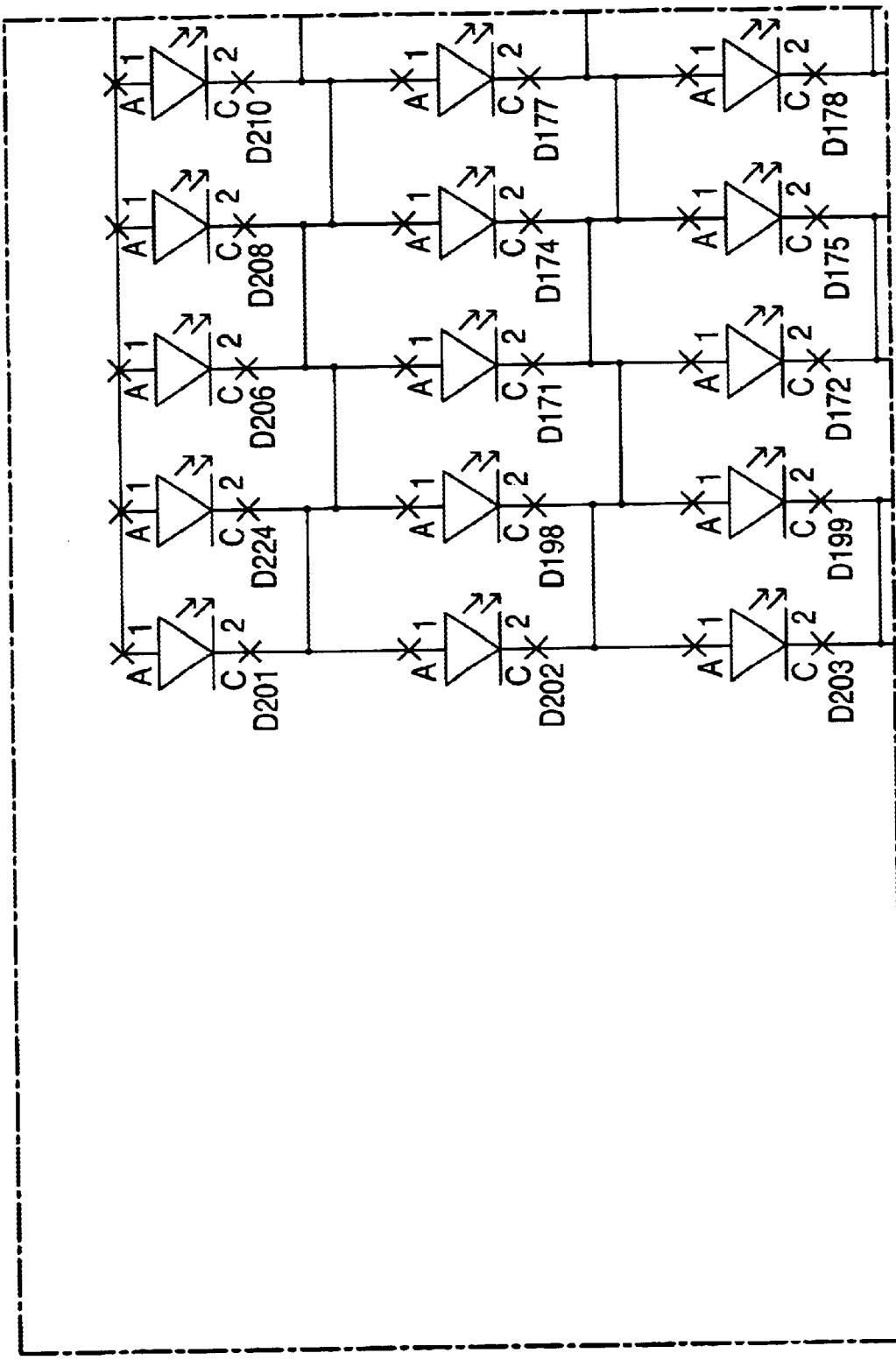
Figure 4I:
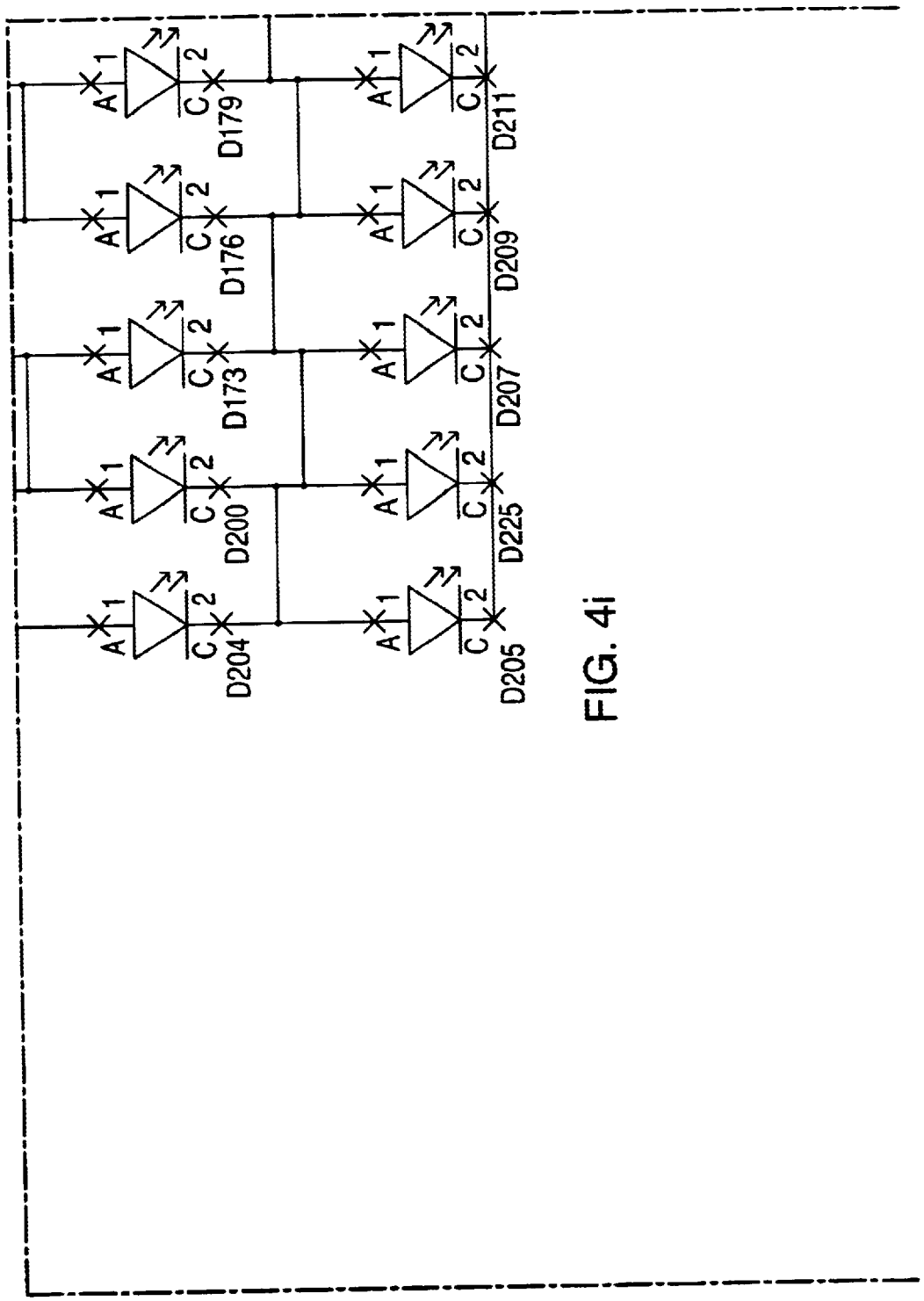
Figure 4J:
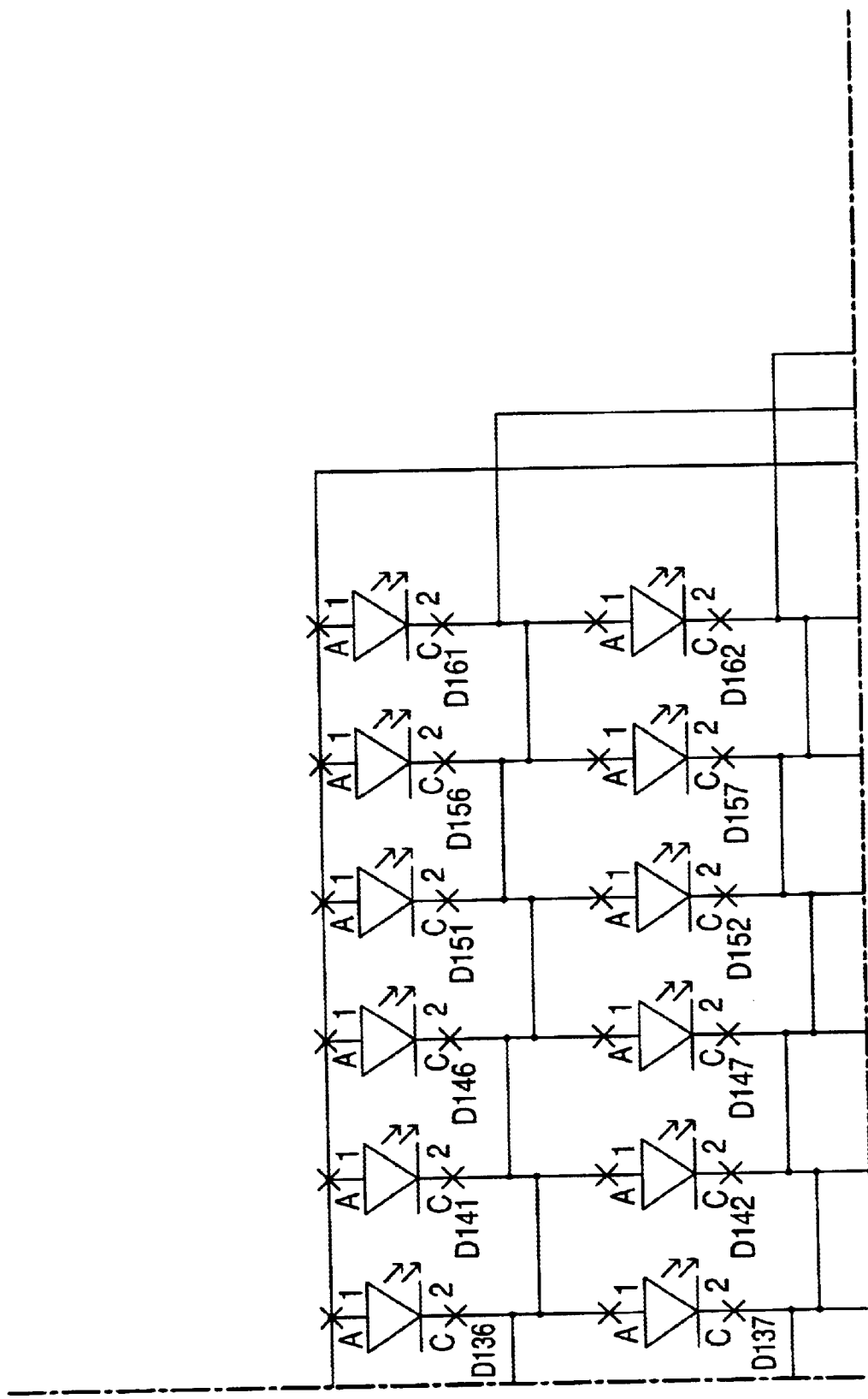
Figure 4K:
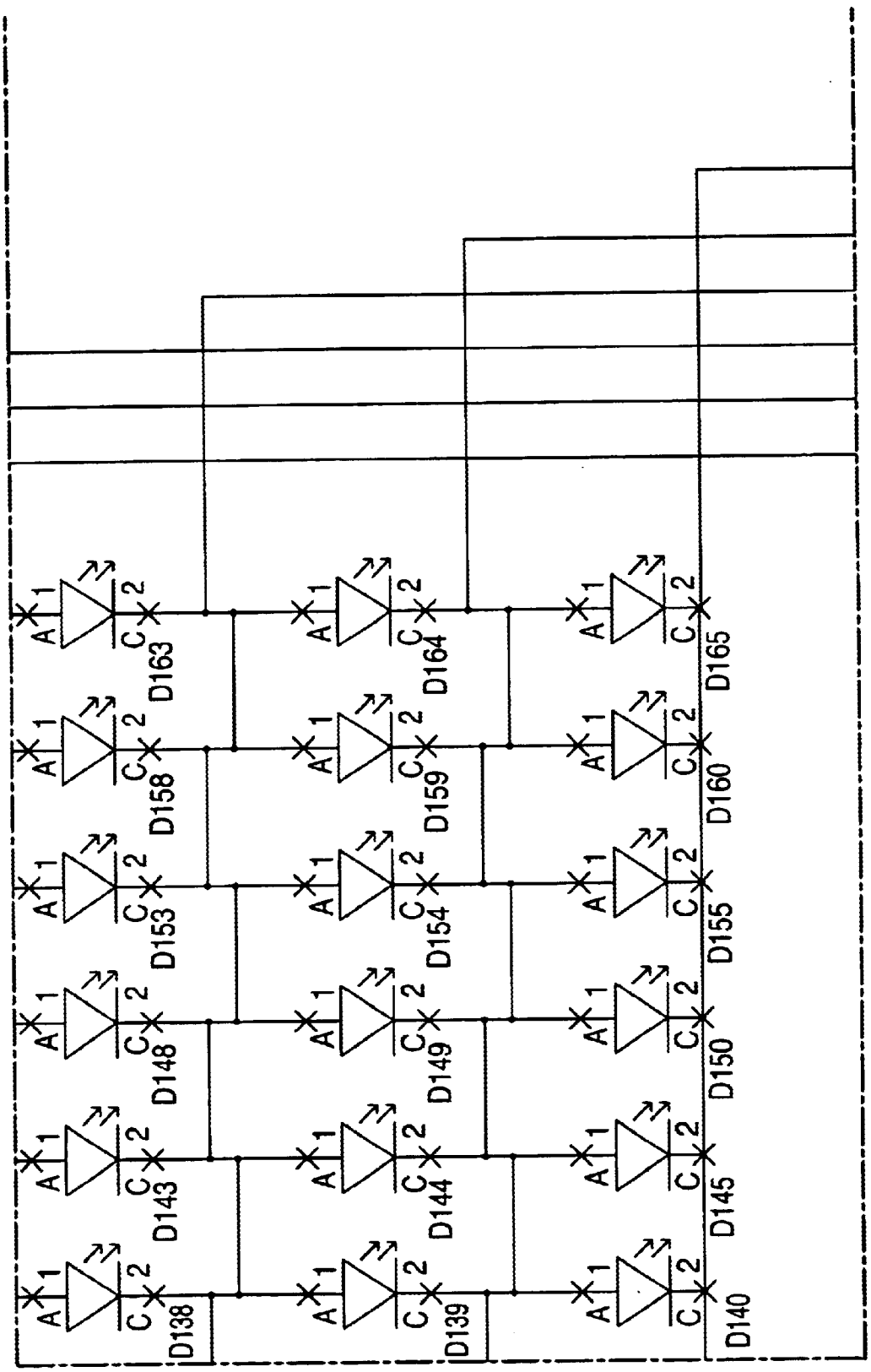
Figure 41:
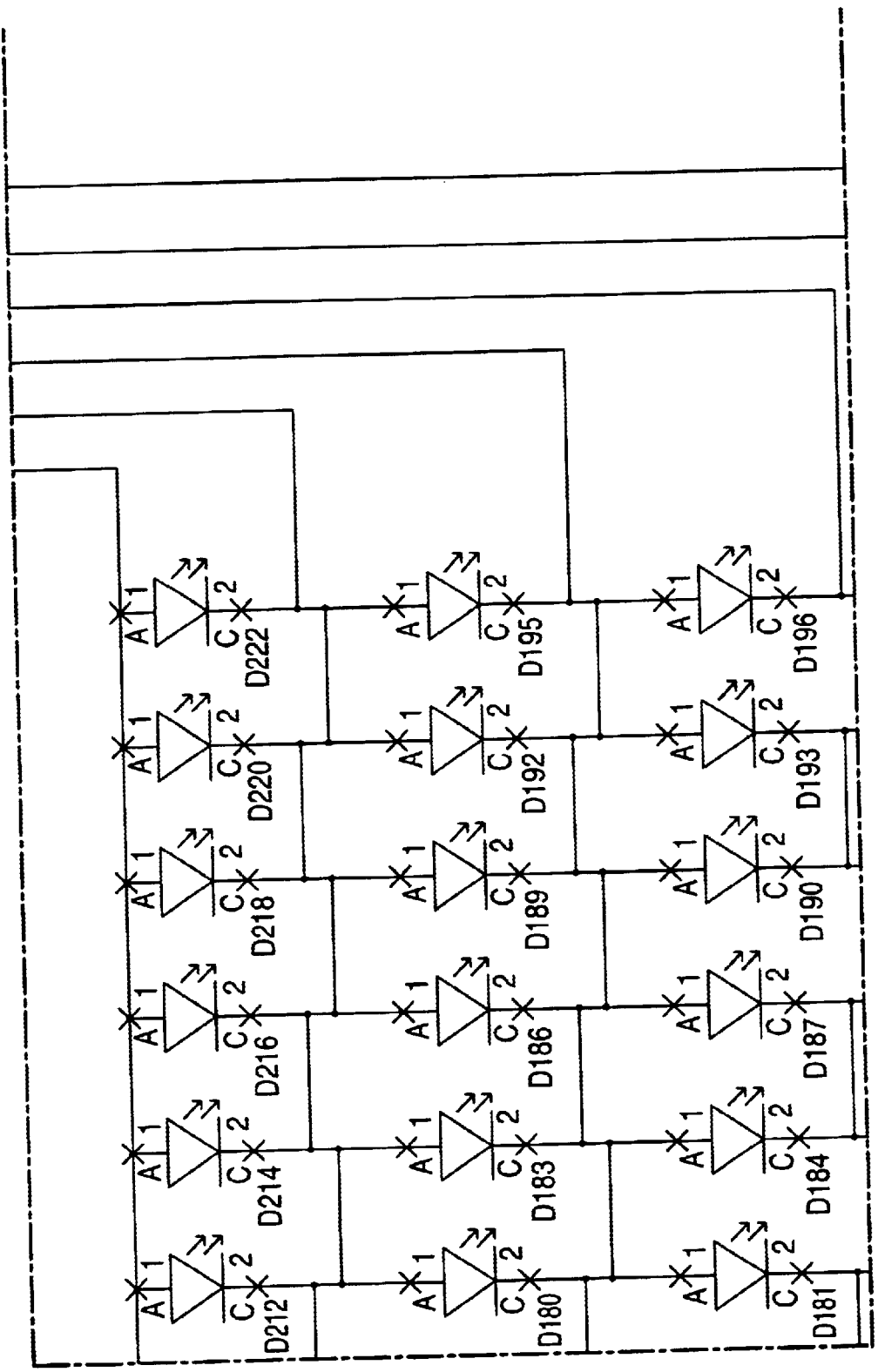
Figure 4M:
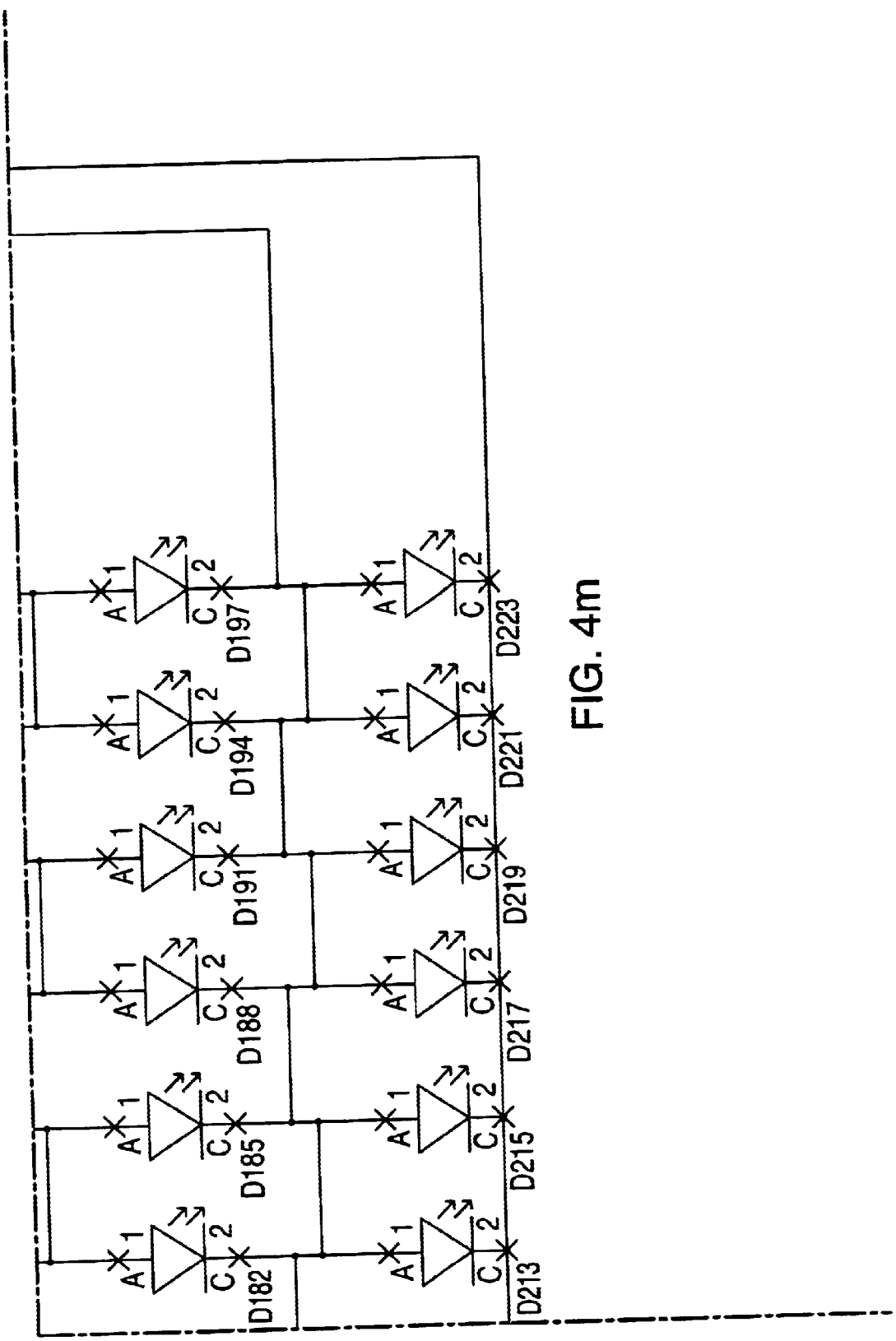

In FIG. 2, apparatus 20 is a typical LED head. The LED head 20 has a body 21 that can be a plurality of shapes. A signal cable 22 provides the required signal from the controller to the LED head 20 and is connected to the body 21 at any location depending upon the design of the LED head 20. The internal portion 41 of body 21 is formed to accept the platform 23, a matrix plate 28, and a retainer 30. The matrix plate 28 is a permanent member. Furthermore a member 29 that can be a diffuser, window, or polarizer may be mounted over the matrix plate 28 for different effects. The platform 23 is normally a printed circuit board. The platform 23 is positioned within the internal portion 41 of body 21 before the matrix plate 28 against the internal top 42 and internal side 46 of body 21 and can be a plurality of shapes. However, the first side 38 is parallel to the second side 39 of platform 23. The first side 38 of platform 23 touches the internal top 42 and internal side 46 of body 21 with platform 23 sliding easily into the internal portion of body 21. Top 43 and bottom 44 are parallel in body 21. The outer side 45 is parallel with lip 40, and lip 40 is slightly recessed from the outer side 45. The matrix plate 28 is formed and positioned against bottom 44 and can be a plurality of shapes. However, the first side 34 and second side 35 are parallel with the first side touching bottom 44 of body 21. The internal portion 37 of matrix plate 28 is formed to allow light to pass through from the LED cluster 26 that is mounted on the second side 39 of platform 23. Finally, a retainer 30, that can be a plurality of shapes, has an outside portion 47 that mates with the inside portion 36 of matrix plate 28. A first side 31 is parallel to a second side 32 of retainer 30 with the inside portion 33 formed to allow light to pass through from the LED cluster 26. The retainer 30 is formed to snap fit holding matrix plate 28 and platform 23 inside of the body 21.

Populated in each LED head 20 is a representative LED 27 that can produce various wavelength or colored light which is located on platform 28 that is coupled both mechanically and optically to a photosensitive device 24. The preferable photosensitive device 24 may be a photodiode. As the photosensitive device receives incident light from the populace representative LED 27 it will conduct current. The Ultra LX Interface controller biases the photosensitive device 24 in photovoltaic mode to produce an analog voltage that represents the output light of the representative LED 27. This representative LED 27 will behave similarly to that of the populace in the LED head 20. As the efficiency of the LED cluster 26 changes due to age or changes in temperature the representative LED 27 will change in the same way. The light value is read into the Ultra LX Interface controller and adjusts the current control voltage accordingly. In addition to the photosensitive device 24 there is populated on the platform 23 a temperature-measuring device 25 that may be a thermistor. The device 25 is biased so that as the temperature in the LED head 20 increases its analog voltage also increases. This temperature voltage can be used to indicate high temperature levels for the LED head 20 and/or compensate the light measurement because of the effects of temperature on the LED head 20. The temperature voltage can also be used with other parameters programmed into the Ultra LX Interface to give, for example, an early indication of the end of the life of the LED head 20.

Referring to FIGS. 3 and 4, the wiring schematic 50 and wiring schematic 60 of each LED head is a matrix configuration. This configuration allows for minimization of change in overall light output upon the failure of a LED in the head. This matrix prevents failure when the LED is opened, when the LED is shorted, and when the LED is partially shorted. The opened LED would usually be caused as a result of a manufacturing problem. For example, no solder paste was applied to the pad and consequently no connection. The current supplied to that LED would then divert to the LED's in parallel with it and become brighter thus compensating the decrease in overall light output caused by the open circuit. A shorted LED would usually be caused as a result of a manufacturing problem. For example, too much solder paste was applied to the pad and consequently causing a solder bridge. All current supplied to the LED head would flow down this one short. No light would be emitted from the entire row of LED's that contain the short. The LED head voltage output from the Ultra LX Interface controller could then be used to sense the change, identify the error and/or provide enough current to stabilize the total light output from the LED head in the amount that would be provided had not an entire row of LEDs shorted. When there is a partially shorted LED, the Ultra LX Interface controller senses the small change in voltage, identifies the error and/or provides the proper amount of current to stabilize the total light output from the LED head in the amount that would be provided had there not been a partial short.

The intelligent controller 12, as shown in FIG. 1, provides the system control of the LED head 13. The control system consists of optical feedback stabilization, temperature compensation, and LED head 13 failure detection and indication.

A photosensitive device 24, as shown in FIG. 2, such as a photodiode, is configured to collect a large proportion of the light output from one LED of the LED cluster or a representative proportion of light from a number of LED's. The photocurrent generated is used as the regulation parameter in an intelligent controller 12 driving the LED array (cluster) 26 as shown in FIG. 2. Using the intelligent controller 12 can compensate for the aging and temperature effects in an LED head 13. The photosensitive device with its coupled LED cluster are electrically interconnected as part of the LED head array. Furthermore, the photosensitive device should be positioned to be optically isolated from the main LED array. This may be accomplished by positioning, for example, a photodiode 24 and coupled LED 27, as shown in FIG. 2, or within a mechanical recess when one is designed into the platform 23. Optically isolating the photodiode avoids the detrimental effects of object reflections being received by the photodiode and being misinterpreted as LED output variations by the intelligent controller 12.

However, the photosensitive device 24 is not required to be optically isolated for it to work.

The monitoring of LED temperatures through the use of a temperature-sensitive device 25 that can be a thermistor, as shown in FIG. 2, enables the intelligent controller to carry different control scenarios. First, compensation for changes, for example, in photodiode performance, because of temperature. Second, application of the forward current versus temperature derating curve for the LED, so that the intelligent controller can both limit the forward current and provide an indicator light that it is doing so, and hence override the optical feedback control. Finally, monitoring temperature allows by software prediction of the end-of-life for the LED cluster 26.

The continuous monitoring of LED current in the LED head 20, as shown in FIG. 2, allows for the detection of spontaneous or very short-term current changes that accompany catastrophic LED cluster 26 failure. The intelligent controller 12 as shown in FIG. 1 would accomplish this. These changes of turn-on current are detected from a comparison to the last time the LED cluster 26 was turned on. The LED failure detection by current monitoring can be enhanced by a suitable choice of LED cluster 26 interconnection such that the failure of one LED has the maximum effect on the monitored current.

While there has been illustrated and described what is at present considered to be the preferred embodiment of the claimed invention, it will be appreciated that numerous changes and modifications are likely to occur to those skilled in the art. It is intended in the appended claims to cover all those changes and modifications that fall within the spirit and scope of the claimed invention.

What is claimed is:

1. A light emitting diode lighting apparatus, comprising:
   a) a power supply for providing a fixed direct current;
   b) a light emitting diode head for emitting light;
   c) sensor means for detecting at least one head parameter, said sensor means producing at least one signal corresponding to said at least one head parameter;
   d) a controller for adjusting the level of said light output on said head in response to at least one signal.

2. The light emitting diode lighting apparatus as claimed in claim 1, wherein said controller is an intelligent controller.

3. The light emitting diode lighting apparatus as claimed in claim 1, wherein said head is powered from constant voltage.

4. The light emitting diode lighting apparatus as claimed in claim 2, wherein said intelligent controller supplies stable current through a (0–5 v dc) analog input voltage such that said controller adjusts said current in response to changes in said at least one head parameter.

5. The light emitting diode lighting apparatus as claimed in claim 4, wherein said intelligent controller provides a light level output analog voltage, an operating temperature output analog voltage and a light emitting diode head forward output analog voltage.

6. The light emitting diode lighting apparatus as claimed in claim 1, wherein said power supply provides about 12 v dc output voltage.

7. A light emitting diode head apparatus, comprising:
   a) a body that is internally hollow for positioning a light emitting diode cluster inside said body and communicating with a signal cable;
   b) a light emitting diode cluster mounted on a platform for emitting a desired level of light;
   c) a photosensitive device for collecting a representative amount of light from a number of light emitting diodes and for generating a photocurrent signal to drive said cluster through an intelligent controller with said photosensitive device mounted on said platform and optically isolated from said light emitting diode cluster;
   d) a temperature-sensitive device for monitoring temperature of said cluster and for generating an operating temperature signal to drive said cluster through an intelligent controller with said temperature device located within said cluster;
   e) a light emitting diode failure detector for continuous monitoring of light emitting diode current allowing the detection of short term current changes and providing a signal to drive said cluster through an intelligent controller;
   f) a matrix plate to hold said light emitting diode cluster in said body; and
   g) a retainer to hold other members and said matrix plate in said body.

8. The light emitting diode lighting head apparatus as claimed in claim 7, wherein said light emitting diode cluster further comprises a plurality of light emitting diodes mounted on a platform with said photosensitive device mounted within a mechanical recess formed on same side as the light emitting diode cluster is mounted on said platform.

9. The light emitting diode lighting head apparatus as claimed in claim 7, wherein said body material is selected from the group consisting of plastic, PVC, and metal.

10. The light emitting diode lighting head apparatus as claimed in claim 7, wherein said other members are selected from the group consisting of a diffuser, a window, and a polarizer.

11. The light emitting diode lighting head apparatus as claimed in claim 7, wherein said temperature-sensitive device is a thermistor.

12. The light emitting diode lighting head apparatus as claimed in claim 10, wherein said plate material is selected from the group consisting of plastic, glass, PVC, and metal.

13. The light emitting diode lighting head apparatus as claimed in claim 7, wherein said failure detector indicates a signal selected from the group consisting of an open circuit, a short circuit, a partial emitting diode, and a resistive diode.

14. The light emitting diode lighting head apparatus as claimed in claim 12, wherein said retaining ring material is selected from the group consisting of plastic, glass, PVC, and metal.

15. The light emitting diode lighting head apparatus as claimed in claim 7, wherein said light emitting diode cluster further comprises a plurality of light emitting diodes mounted on a platform with said photosensitive device mounted on the opposite side of said platform.

16. The light emitting diode lighting head apparatus as claimed in claim 15, wherein said light emitting diode cluster further comprises a plurality of light emitting diodes mounted on a platform with said temperature sensing device mounted on the same side of said platform and among the cluster of light emitting diodes.

17. The light emitting diode lighting head apparatus as claimed in claim 7, wherein said photosensitive device is a photodiode.

18. The light emitting diode lighting head apparatus as claimed in claim 15, wherein said light emitting diode cluster further comprises a plurality of light emitting diodes providing said light with a plurality of colors.

19. A light emitting diode head apparatus, comprising:
   a) a body that is internally hollow for positioning a light emitting diode cluster inside said body and communicating with a signal cable;

b) a light emitting diode cluster mounted on a platform for emitting a desired level of light;

c) an isolated LED for emitting light in conjunction with said cluster;

d) a photosensitive device for collecting a representative amount of light from a number of light emitting diodes and for generating a photocurrent signal to drive said cluster through an intelligent controller with said photosensitive device mounted on said platform and optically isolated from said light emitting diode cluster and coupled with said isolated LED;

e) a temperature-sensitive device for monitoring the temperature of said cluster and for generating an operating temperature signal to drive said cluster through an intelligent controller with said temperature-sensitive device located within said cluster;

f) a light emitting diode failure detector for continuous monitoring of light emitting diode current allowing the detection of short term current changes and providing a signal to drive said cluster through an intelligent controller.

* * * * *